United States Patent [19]

Murata et al.

[11] Patent Number: 5,892,075

[45] Date of Patent: Apr. 6, 1999

[54] PROCESS FOR SYNTHESIZING METALLOCENE COMPOUNDS

[75] Inventors: Kunihiko Murata; Junichi Hori; Masahiro Yoshida, all of Saitama-ken, Japan

[73] Assignee: Kanto Kagaku Kabushiki Kaisha, Tokyo, Japan

[21] Appl. No.: 936,169

[22] Filed: Sep. 23, 1997

[30] Foreign Application Priority Data

Oct. 4, 1996 [JP] Japan .................................. 8-281644

[51] Int. Cl.$^6$ .............................. C07F 17/00; C07F 7/00
[52] U.S. Cl. .................................. 556/9; 556/11; 556/12; 556/53; 556/54; 556/56; 502/103; 502/117; 526/160; 526/943
[58] Field of Search .................................. 556/9, 11, 12, 556/53, 54, 56; 526/943, 160; 502/103, 117

[56] References Cited

U.S. PATENT DOCUMENTS

| | | |
|---|---|---|
| 5,103,030 | 4/1992 | Rohrmann et al. . |
| 5,391,790 | 2/1995 | Rohrmann et al. . |
| 5,495,035 | 2/1996 | Jordan et al. . |
| 5,616,747 | 4/1997 | Rohrmann et al. . |

FOREIGN PATENT DOCUMENTS

| | | |
|---|---|---|
| 1-197490 | 8/1989 | Japan . |
| 6-122692 | 5/1994 | Japan . |
| WO 95/32979 | 12/1995 | WIPO . |

OTHER PUBLICATIONS

J. Am. Chem. Soc., 110, 6255 (1988).
Angew. Chem. Int. Ed. Engl., 24, 507 (1985).
J. Am. Chem. Soc., 109, 6544 (1987).
Chem. Rev., 92, 965 (1992).
Organometallics, 13, 954 (1994).
Organometallics, 13, 964 (1994).
J. Organomet. Chem., 288, 63 (1985).
Japan Chemical Society ed. Organometallic complex (4th ed. Experimental chemistry series No. 18), Maruzen (1991) p. 81 with an abridged English translation.
J. Organomet. Chem., 232, 233 (1982).
J. Organomet. Chem., 369, 359 (1989).
Chem. Lett., 1853 (1989).
Organometallics, 10, 1501 (1991).
J. Organomet. Chem., 415, 75 (1991).
J. Organomet. Chem., 497, 43 (1995).
J. Organomet. Chem., 342, 21 (1988).
Organometallics, 11, 1869 (1992).
Organometallics, 10, 2349 (1991).
Organometallics, 10, 2998 (1991).
Organometallics, 12, 2879 (1993).
Organometallics, 12, 4391 (1993).
Organometallics, 14, 5 (1995).
J. Am. Chem. Soc., 118, 8024 (1996).
JP, B, 42–22691 with an abridged English translation.
Organometallics, 13, 2907 (1994).
Z. Anorg. Allg. Chem., 621, 2021, (1995).
Spectrochimica Acta., 24A, 1213 (1968).
211th American Chemical Society National Meeting, Division of Polymer Chemistry Inc. 251.
J. Organomet. Chem., 535, 29 (1997).
Gary M. Diamond, et al., Synthesis of Group 4 Metal rac–(EBI)M(NR)$_2)_2$ Complexes by Amine Elimination. Scope and Limitations, Dept. of Chemistry, University of Iowa, Iowa 52242, Organometallics, 1996, 15, 4030–4037.
Joseph N. Christopher, et al., Synthesis, Structure, and Reactivity of rac–Me$_2$Si(indenyl)$_2$Zr(NMe$_2$)$_2$, Dept. of Chemistry, University of Iowa, Iowa City, Iowa 52242, Organometallics, 1996, 15, 4038–4044.
Gary M. Diamond, et al., Synthesis of Me$_2$Si–Bridged ansa–Zirconocenes by Amine Elimination, Dept. of Chemistry, University of Iowa, Iowa City, Iowa 52242, Organometallics, 1996, 15, 4045–4053.

*Primary Examiner*—Porfirio Nazario-Gonzalez
*Attorney, Agent, or Firm*—Darby & Darby

[57] ABSTRACT

The object of the invention resides in the development of an improved process for synthesizing metallocene compounds useful as olefin polymerization catalysts.

A new process for synthesizing metallocene compounds of formulae (IV) and (IV') comprises a reaction of formula (I) with formula (II) or (II') to afford formula (III) or (III'), and then a reaction of a halogenating agent.

In formulae (IV) and (IV') described below, M$^1$ is a group IV transition-metal atom, L$^1$ and L$^2$ can be each other identical or different and are substituted or unsubstituted cyclopentadienyl, substituted or unsubstituted indenyl or substituted or unsubstituted fluorenyl groups, B is a hydrocarbon having 1–20 carbon atoms, silylene having 1–20 carbon atoms, oligosilylene or germylene groups, binding to L$^1$ and L$^2$, Y can be identical or different and is each independently of one another a halogen atom. Further, M$^1$ can be coordinated with an ether or an amine at any coordination number.

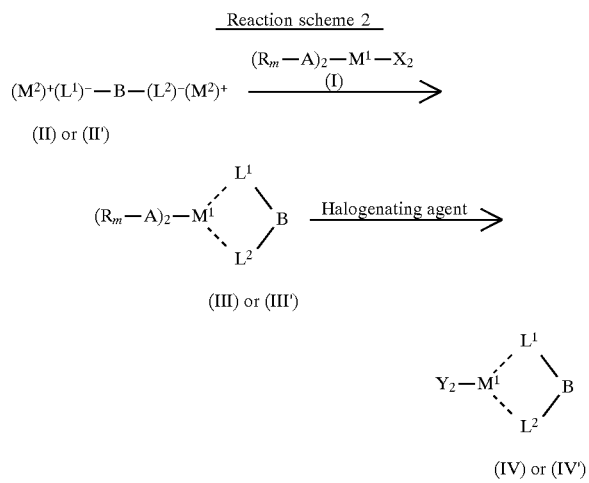

10 Claims, No Drawings

PROCESS FOR SYNTHESIZING METALLOCENE COMPOUNDS

BACKGROUND OF THE INVENTION

The invention relates to a new process for the synthesis of metallocene compounds and the metallocene compounds having a racemic structure, which are useful as a polymerization catalyst for olefins.

Metallocene compounds, in which a cyclopentadienyl, indenyl or fluorenyl groups, or a derivative thereof are made a ligand, are useful as a polymerization catalyst for olefins such as ethylene, propylene or the like under the coexistence of a cocatalyst, for example, aluminoxane. For the preparation for a stereoregular polyolefine have been examined metallocene compounds having various kinds of stereostructures. For a syndiotactic polyolefine preparation is effective a metallocene compound having the Cs symmetry (*J. Am. Chem. Soc.*, 110, 6255 (1988), whereas it is reported that for an isotactic polyolefine preparation is effective a metallocene compound having a racemic structure (*Angew. Chem. Int. Ed. Engl.*, 24, 507 (1985); *J. Am. Chem. Soc.*, 109, 6544 (1987); *Chem. Rev.*, 92, 965 (1992); *Organometallics*, 13, 954 (1994); *Organometallics*, 13, 964 (1994)).

Conventionally, synthesis of a metallocene compound having a racemic structure is shown in Reaction Scheme I described below, and it is carried out by reacting the dianion produced by the deprotonation of the ligand and metal tetrachloride or its tetrahydrofuran adduct.

(Reaction Scheme 1)

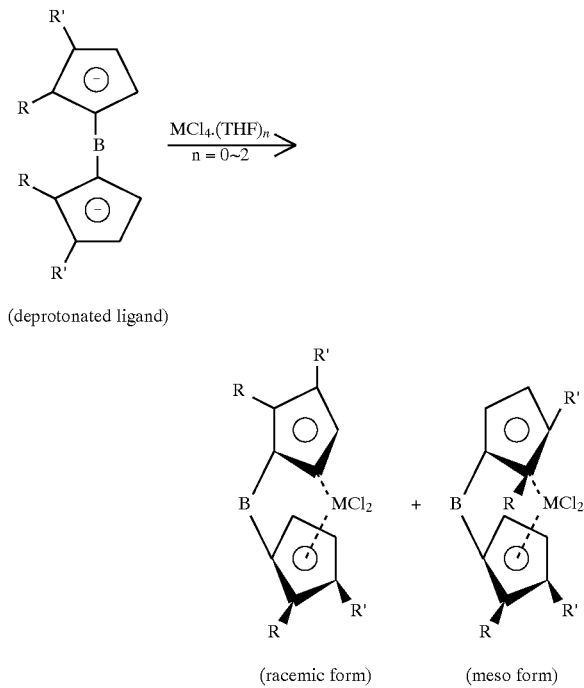

However, since this method gives tarry substances as byproducts, the procedure to separate the aimed metallocene compound having the racemic structure is very complicated (*Angew. Chem. Int. Ed. Engl.*, 24, 507 (1985); *J. Organomet. Chem.*, 288, 63 (1985); Japan Chemical Society ed. *Organometallic complex* (4th ed. Experimental chemistry series No. 18), Maruzen (1991) p. 81 (in Japanese)), and in many cases a metallocene compound having a meso structure is produced as a byproduct in nearly same amount, whereby there is such a problem that the separation of the aimed racemic metallocene compound is tedious. Generally, since metallocene compounds having the meso structure decrease the efficiency as a stereoregular polymerization catalyst, they are removed by a combination of purifying operations such as column chromatographic, washing or recrystallizing methods (*J. Organomet. Chem.*, 232, 233 (1982); *J. Organomet. Chem.*, 369, 359 (1989); *Chem. Lett.*, 1853 (1989), *Organometallics*, 10, 1501 (1991); *J. Organomet. Chem.*, 415, 75 (1991); *Organometalllics*, 13, 954 (1994); *J. Organomet. Chem.*, 497, 43 (1995).

Thus, the conventional synthetic methods give a considerable amount of meso metallocene compounds as byproducts, therefore, the yields of racemic metallocene compounds are low, and due to the fact that the procedure in the purification step is tedious, the cost of the synthesis is high, and it is difficult to carry out in an industrial scale.

As a trial for solving the above problems is reported the method that after the reaction only the metallocene compounds having the racemic structure are crystallized appropriately by selecting the reaction solvent (JP, A, 6-122692; U.S. Pat. No. 5,391,790; U.S. Pat. No. 5,616,747), though, in this method the metallocene compound having essentially meso structure is produced in a nearly half amount, therefore, it can hardly be said that this is an efficient synthetic method.

Further, although the methods by which the metallocene compounds having the meso structure are converted to the metallocene compounds having the racemic structure are studied (*J. Organomet. Chem.*, 342, 21 (1988); *Organometallics*, 11, 1869 (1992)), a compound of the enough purity could not be obtained, and furthermore, the decomposition of the metallocene compounds occurred.

On the other hand, the method to selectively synthesize the metallocene compounds having the racemic structure is also reported. In the methods using the ligand in which the bulky substituent is introduced to a cyclopentadienyl skeleton and the ligand having a binaphtyl skeleton in a bridging part, they give low yield and are impractical (*Organometallics*, 10, 2349 (1991); *Organometallics*, 10, 2998 (1991)). The method to carry out the reaction at the low reaction temperature of −78° C. is also proposed (JP, A, 1-197490; U.S. Pat. No. 5,103,030), but the yield expected is not obtained. Further, in the synthetic examples of the metallocene compounds having the pseudo-racemic structure are used the ligand having the special structure in which 2-position of the indenyl group is bridged by the biaryl group, and the method is practically poor (*Organometallics*, 12, 2879 (1993); *Organometallics*, 12, 4391 (1993)). Also, a method employing $(CH_3)_2ZrCl_2$ has been studied, but the selectivity of the racemic structure amounts at most around 75% in this method. Moreover this might cause trouble in that the reaction tends to take place to predominantly form a meso-type depending on the structure of the ligand (*J. Organomet. Chem.*, 535, 29 (1997)).

On the contrary are reported the methods to obtain the metallocene compounds having the racemic structure in high yield by reacting $Zr(NMe_2)_4$ with the ligand (WO 95/32979; U.S. Pat. No. 5,495,035; *Organometallics*, 14, 5 (1995); *J. Am. Chem. Soc.*, 118, 8024 (1996)). However, these methods require such a long time as 3–24 hours at the reaction temperature of 80°–160° C., usually 100° C. In the reaction condition, in which heating is done for long time like this, there is a possibility of the polymerization or the decomposition of a ligand which is unstable for heat, and due to the fact that dimethylamine, the starting material of $Zr(NMe_2)_4$, is a gas (b.p. 7° C.) at room temperature, a special reaction equipment corresponding to the gas reaction to prepare $Zr(NMe_2)_4$ is necessary. Further, on the treatment there are various kinds of problems such that $Zr(NMe_2)_4$ is very unstable for air.

SUMMARY OF THE INVENTION

Under these circumstances, the inventors made an intensive studies to synthesize metallocene compounds having the racemic structure and succeeded in developing a new process for the synthesis of metallocene compounds, whereby it is simple in the treatment and furthermore suitable for the synthesis of metallocene compounds having the racemic structure in high yields. The invention is based on this finding.

The invention provides four new synthetic methods of metallocene compounds described in 1)–4) below.

1) New process for synthesizing metallocene compounds of the below general formula (III) comprising that IV group transition-metal compounds of the general formula (I)

$$(R_m\text{---}A)_2\text{---}M^1\text{---}X_2 \qquad (I)$$

(wherein $M^1$ is a group IV transition-metal atom, A can be identical or different and is each independently of one another a hetero atom, R can be identical or different and is each independently of one another a hydrocarbon group having 1–30 carbon atoms, whereby each of R binds one another to constitute a ring containing A, or A and $M^1$, X can be identical or different and is each independently of one another a halogen atom or an alkoxy group having 1–10 carbon atoms, and m is 1 or 2. Further, $M^1$ can be also coordinated with an ether or an amine at any coordination number.) and compounds of the general formula (II)

$$(M^2)^+(L^1)^-\text{---}B\text{---}(L^2)^-(M^2)^+ \qquad (II)$$

(wherein $L^1$ and $L^2$ can be each other identical or different and are a cyclopentadienyl, substituted cyclopentadienyl, indenyl, substituted indenyl, fluorenyl or substituted fluorenyl groups, B is a hydrocarbon having 1–20 carbon atoms, silylene having 1–20 carbon atoms, oligosilylene or germylene groups, binding to $L^1$ and $L^2$, $M^2$ is an alkaline or alkaline earth metals. Further, $M^2$ can be coordinated with an ether or an amine at any coordination number.) are reacted to afford metallocene compounds of the general formula (III)

(wherein $M^1$ is a group IV transition-metal atom, A can be identical or different and is each independently of one another a hetero atom, R can be identical or different and is each independently of one another a hydrocarbon group having 1–30 carbon atoms, whereby each of R binds one another to constitute a ring containing A, or A and $M^1$, $L^1$ and $L^2$ can be each other identical or different and a cyclopentadienyl, substituted cyclopentadienyl, indenyl, substituted indenyl, fluorenyl or substituted fluorenyl groups, B is a hydrocarbon having 1–20 carbon atoms, silylene having 1–20 carbon atoms, oligosilylene or germylene groups, binding to $L^1$ and $L^2$, and m is 1 or 2. Further, $M^1$ can be coordinated with an ether or an amine at any coordination number.)

2) New process for synthesizing halogenated metallocene compounds of the below general formula (IV) comprising that the compounds of the general formula (III)

(wherein each abbreviation has the same meaning as described above) are halogenated to afford the compounds of general formula (IV)

(wherein $M^1$ is a group IV transition-metal atom, $L^1$ and $L^2$ can be each other identical or different and are a cyclopentadienyl, substituted cyclopentadienyl, indenyl, substituted indenyl, fluorenyl or substituted fluorenyl groups, B is a hydrocarbon having 1–20 carbon atoms, silylene having 1–20 carbon atoms, oligosilylene or germylene groups, binding to $L^1$ and $L^2$, Y can be identical or different and is each independently of one another a halogen atom. Further, $M^1$ can be coordinated with an ether or an amine at any coordination number.).

3) New process for synthesizing metallocene compounds of the below general formula (III') having a racemic structure comprising that group IV transition-metal compounds of the general formula (I)

$$(R_m\text{---}A)_2\text{---}M^1\text{---}X_2 \qquad (I)$$

(wherein each abbreviation has the same meaning as described above) and compounds of the general formula (II')

$$(M^2)^+(L^1)^-\text{---}B\text{---}(L^2)^-(M^2)^+ \qquad (II')$$

(wherein $L^1$ and $L^2$ can be each other identical or different and are a substituted cyclopentadienyl, indenyl, substituted indenyl or substituted fluorenyl groups, B is a hydrocarbon having 1–20 carbon atoms, silylene having 1–20 carbon atoms, oligosilylene or germylene groups, binding to $L^1$ and $L^2$, $M^2$ is an alkaline or alkaline earth metals. Further, $M^2$ can be coordinated with an ether or an amine at any coordination number.) are reacted to afford metallocene compounds of the general formula (III')

(wherein $M^1$ is a group IV transition-metal atom, A can be identical or different and is each independently of one another a hetero atom, R can be identical or different and is each independently of one another a hydrocarbon group having 1–30 carbon atoms, whereby each of R binds one another to constitute a ring containing A, or A and $M^1$, $L^1$ and $L^2$ can be each other identical or different and a substituted cyclopentadienyl, indenyl, substituted indenyl or substituted fluorenyl groups, B is a hydrocarbon having 1–20 carbon atoms, silylene having 1–20 carbon atoms, oligosilylene or germylene groups, binding to $L^1$ and $L^2$, and m is 1 or 2. Further, $M^1$ can be coordinated with an ether or an amine at any coordination number.).

4) New process for synthesizing halogenated metallocene compounds of the below general formula (IV') having a racemic structure comprising that the compounds of the general formula (III')

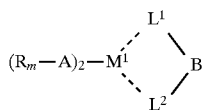

(III')

(wherein each abbreviation has the same meaning as described above) are halogenated to afford the compounds of general formula (IV')

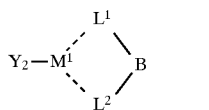

(IV')

(wherein $M^1$ is a group IV transition-metal atom, $L^1$ and $L^2$ can be each other identical or different and are a substituted cyclopentadienyl, indenyl, substituted indenyl or substituted fluorenyl groups, B is a hydrocarbon having 1–20 carbon atoms, silylene having 1–20 carbon atoms, oligosilylene or germylene groups, binding to $L^1$ and $L^2$, Y can be identical or different and is each independently of one another a halogen atom. Further, $M^1$ can be coordinated with an ether or an amine at any coordination number.).

In the following, the invention will be explained in detail.

Usually, the synthesis of metallocene compounds is carried out by reacting group IV transition-metal compounds having four same leaving groups (Illustrative of an example are zirconium tetrachloride or tetrakisdimethylamido zirconium.) with a compound of the general formula (II) or (II'), or with a ligand which is not deprotonated. To the contrary, the invention is the method that a compound of the general formula (II) or (II') is reacted with a compound of the general formula (I) to give the compounds of the general formula (III) or (III'), which are converted further to the compounds of the general formula (IV) or (IV') (see Reaction Scheme 2). This type reaction of a compound of the general formula (I) with a compound of the general formula (II) or (II') (is a new reaction. Further, in the reaction of the compounds represented by the general formula (I) and (II'), metallocene compounds having the racemic structure can be synthesized in high yields, and the method is industrially very useful.

The concept of the invention resides in an efficient synthesis of metallocene compounds in general, particularly the metallocene compounds having a racemic structure by employing group IV transition-metal compounds not having four leaving groups but having both two leaving groups and two other groups containing hetero atoms, so as to proceed with a mild complex formation reaction, and to suppress byproducts' formation, and further to realize a face selectivity in the complex formation.

Thus, the characteristics of the invention are that the compounds of the general formula (I), that is, the group IV transition-metal compounds having both two leaving groups and two other groups containing hetero atoms are used as a starting material and as to the part of an organic group which constitutes a group containing a hetero atom, there is no restriction for its structure in the case that a hydrocarbon group has 1–30 carbon atoms. Similarly, as to the part of a hetero atom which constitutes the group containing the hetero atom, it is not restricted to specific hetero atoms such as nitrogen, oxygen, phosphorus or sulfur atoms.

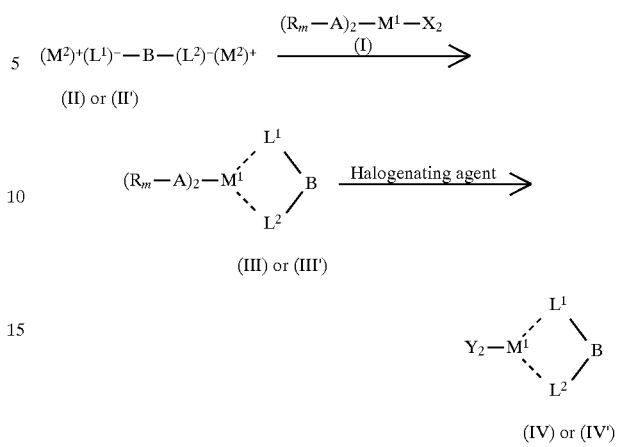

Reaction scheme 2

Illustrative of the compounds of the general formula (I) are, for example, bis(dimethylamido)titanium difluoride, bis (diethylamido)titanium difluoride, bis(dipropylamido) titanium difluoride, bis(dibutylamido)titanium difluoride, bis((N-methyl)ethylamido)titanium difluoride, bis((N-methyl)propylamido)titanium difluoride, bis((N-methyl) butylamido)titanium difluoride, bis((N-ethyl)propylamido) titanium difluoride, bis((N-ethyl)butylamido)titanium difluoride, bis(piperidido)titanium difluoride, bis (pyrrolidido)titanium difluoride, bis(pyrroleyl)titanium difluoride, bis(N-methylcyclohexylamido)titanium difluoride, bis(N-methylanilido)titanium difluoride, bis(N-ethylanilido)titanium difluoride, bis(N-propylanilido) titanium difluoride, bis(N-butylanilido)titanium difluoride, bis((N-methyl)toluylamido)titanium difluoride, bis((N-ethyl)toluylamido)titanium difluoride, bis((N-propyl) toluylamido)titanium difluoride, bis((N-butyl)toluylamido) titanium difluoride, bis((N-methyl)dimethylphenylamido) titanium difluoride, bis((N-ethyl)dimethylphenylamido) titanium difluoride, bis((N-propyl)dimethylphenylamido) titanium difluoride, bis((N-butyl)dimethylphenylamido) titanium difluoride, bis(diphenylamido)titanium difluoride, bis((N-phenyl)toluylamido)titanium difluoride, bis (ditoluylamido)titanium difluoride, N,N'-diphenylmethylenediamidotitanium difluoride, N,N'-diphenylethylenediamidotitanium difluoride, N,N'-diphenylpropylenediamidotitanium difluoride, bis (dimethylamido)zirconium difluoride, bis(diethylamido) zirconium difluoride, bis(dipropylamido)zirconium difluoride, bis(dibutylamido)zirconium difluoride, bis((N-methyl)ethylamido)zirconium difluoride, bis((N-methyl) propylamido)zirconium difluoride, bis((N-methyl) butylamido)zirconium difluoride, bis((N-ethyl) propylamido)zirconium difluoride, bis((N-ethyl) butylamido)zirconium difluoride, bis(piperidido)zirconium difluoride, bis(pyrrolidido) zirconium difluoride, bis (pyrroleyl) zirconium difluoride, bis(N-methylcyclohexylamido)zirconium difluoride, bis(N-methylanilido)zirconium difluoride, bis(N-ethylanilido) zirconium difluoride, bis(N-propylanilido)zirconium difluoride, bis(N-butylanilido)zirconium difluoride, bis((N-methyl)toluylamido)zirconium difluoride, bis((N-ethyl) toluylamido)zirconium difluoride, bis((N-propyl) toluylamido)zirconium difluoride, bis((N-butyl) toluylamido)zirconium difluoride, bis((N-methyl) dimethylphenylamido)zirconium difluoride, bis((N-ethyl) dimethylphenylamido)zirconium difluoride, bis((N-propyl)

dimethylphenylamido)zirconium difluoride, bis((N-butyl) dimethylphenylamido)zirconium difluoride, bis(diphenylamido)zirconium difluoride, bis((N-phenyl)toluylamido)zirconium difluoride, bis(ditoluylamido)zirconium difluoride, N,N'-diphenylmethylenediamidozirconium difluoride, N,N'-diphenylethylenediamidozirconium difluoride, N,N'-diphenylpropylenediamidozirconium difluoride, bis(dimethylamido)hafnium difluoride, bis(diethylamido)hafnium difluoride, bis(dipropylamido)hafnium difluoride, bis(dibutylamido)hafnium difluoride, bis((N-methyl)ethylamido)hafnium difluoride, bis((N-methyl)propylamido)hafnium difluoride, bis((N-methyl)butylamido)hafnium difluoride, bis((N-ethyl)propylamido)hafnium difluoride, bis((N-ethyl)butylamido)hafnium difluoride, bis(piperidido)hafnium difluoride, bis(pyrrolidido)hafnium difluoride, bis(pyrroleyl)hafnium difluoride, bis(N-methylcyclohexylamido)hafnium difluoride, bis(N-methylanilido)hafnium difluoride, bis(N-ethylanilido)hafnium difluoride, bis(N-propylanilido)hafnium difluoride, bis(N-butylanilido)hafnium difluoride, bis((N-methyl)toluylamido)hafnium difluoride, bis((N-ethyl)toluylamido)hafnium difluoride, bis((N-propyl)toluylamido)hafnium difluoride, bis((N-butyl)toluylamido)hafnium difluoride, bis((N-methyl)dimethylphenylamido)hafnium difluoride, bis((N-ethyl)dimethylphenylamido)hafnium difluoride, bis((N-propyl)dimethylphenylamido)hafnium difluoride, bis((N-butyl)dimethylphenylamido)hafnium difluoride, bis(diphenylamido)hafnium difluoride, bis((N-phenyl)toluylamido)hafnium difluoride, bis(ditoluylamido)hafnium difluoride, N,N'-diphenylmethylenediamidohafnium difluoride, N,N'-diphenylethylenediamidohafnium difluoride, N,N'-diphenylpropylenediamidohafnium difluoride, bis(dimethylamido)titanium dichloride, bis(diethylamido)titanium dichloride, bis(dipropylamido)titanium dichloride, bis(dibutylamido)titanium dichloride, bis((N-methyl)ethylamido)titanium dichloride, bis((N-methyl)propylamido)titanium dichloride, bis((N-methyl)butylamido)titanium dichloride, bis((N-ethyl)propylamido)titanium dichloride, bis((N-ethyl)butylamido)titanium dichloride, bis(piperidido)titanium dichloride, bis(pyrrolidido)titanium dichloride, bis(pyrroleyl)titanium dichloride, bis(N-methylcyclohexylamido)titanium dichloride, bis(N-methylanilido)titanium dichloride, bis(N-ethylanilido)titanium dichloride, bis(N-propylanilido)titanium dichloride, bis(N-butylanilido)titanium dichloride, bis((N-methyl)toluylamido)titanium dichloride, bis((N-ethyl)toluylamido)titanium dichloride, bis((N-propyl)toluylamido)titanium dichloride, bis((N-butyl)toluylamido)titanium dichloride, bis((N-methyl)dimethylphenylamido)titanium dichloride, bis((N-ethyl)dimethylphenylamido)titanium dichloride, bis((N-propyl)dimethylphenylamido)titanium dichloride, bis((N-butyl)dimethylphenylamido)titanium dichloride, bis(diphenylamido)titanium dichloride, bis((N-phenyl)toluylamido)titanium dichloride, bis(ditoluylamido)titanium dichloride, N,N'-diphenylmethylenediamidotitanium dichloride, N,N'-diphenylethylenediamidotitanium dichloride, N,N'-diphenylpropylenediamidotitanium dichloride, bis(dimethylamido)zirconium dichloride, bis(diethylamido)zirconium dichloride, bis(dipropylamido)zirconium dichloride, bis(dibutylamido)zirconium dichloride, bis((N-methyl)ethylamido)zirconium dichloride, bis((N-methyl)propylamido)zirconium dichloride, bis((N-methyl)butylamido)zirconium dichloride, bis((N-ethyl)propylamido)zirconium dichloride, bis((N-ethyl)butylamido)zirconium dichloride, bis(piperidido)zirconium dichloride, bis(pyrrolidido)zirconium dichloride, bis(pyrroleyl)zirconium dichloride, bis(N-methylcyclohexylamido)zirconium dichloride, bis(N-methylanilido)zirconium dichloride, bis(N-ethylanilido)zirconium dichloride, bis(N-propylanilido)zirconium dichloride, bis(N-butylanilido)zirconium dichloride, bis((N-methyl)toluylamido)zirconium dichloride, bis((N-ethyl)toluylamido)zirconium dichloride, bis((N-propyl)toluylamido)zirconium dichloride, bis((N-butyl)toluylamido)zirconium dichloride, bis((N-methyl)dimethylphenylamido)zirconium dichloride, bis((N-ethyl)dimethylphenylamido)zirconium dichloride, bis((N-propyl)dimethylphenylamido)zirconium dichloride, bis((N-butyl)dimethylphenylamido)zirconium dichloride, bis(diphenylamido)zirconium dichloride, bis((N-phenyl)toluylamido)zirconium dichloride, bis(ditoluylamido)zirconium dichloride, N,N'-diphenylmethylenediamidozirconium dichloride, N,N'-diphenylethylenediamidozirconium dichloride, N,N'-diphenylpropylenediamidozirconium dichloride, bis(dimethylamido)hafnium dichloride, bis(diethylamido)hafnium dichloride, bis(dipropylamido)hafnium dichloride, bis(dibutylamido)hafnium dichloride, bis((N-methyl)ethylamido)hafnium dichloride, bis((N-methyl)propylamido)hafnium dichloride, bis((N-methyl)butylamido)hafnium dichloride, bis((N-ethyl)propylamido)hafnium dichloride, bis((N-ethyl)butylamido)hafnium dichloride, bis(piperidido)hafnium dichloride, bis(pyrrolidido)hafnium dichloride, bis(pyrroleyl)hafnium dichloride, bis(N-methylcyclohexylamido)hafnium dichloride, bis(N-methylanilido)hafnium dichloride, bis(N-ethylanilido)hafnium dichloride, bis(N-propylanilido)hafnium dichloride, bis(N-butylanilido)hafnium dichloride, bis((N-methyl)toluylamido)hafnium dichloride, bis((N-ethyl)toluylamido)hafnium dichloride, bis((N-propyl)toluylamido)hafnium dichloride, bis((N-butyl)toluylamido)hafnium dichloride, bis((N-methyl)dimethylphenylamido)hafnium dichloride, bis((N-ethyl)dimethylphenylamido)hafnium dichloride, bis((N-propyl)dimethylphenylamido)hafnium dichloride, bis((N-butyl)dimethylphenylamido)hafnium dichloride, bis(diphenylamido)hafnium dichloride, bis(N-phenyltoluylamido)hafnium dichloride, bis(ditoluylamido)hafnium dichloride, N,N'-diphenylmethylenediamidohafnium dichloride, N,N'-diphenylethylenediamidohafnium dichloride, N,N'-diphenylpropylenediamidohafnium dichloride, bis(dimethylamido)titanium dibromide, bis(diethylamido)titanium dibromide, bis(dipropylamido)titanium dibromide, bis(dibutylamido)titanium dibromide, bis((N-methyl)ethylamido)titanium dibromide, bis((N-methyl)propylamido)titanium dibromide, bis((N-methyl)butylamido)titanium dibromide, bis((N-ethyl)propylamido)titanium dibromide, bis((N-ethyl)butylamido)titanium dibromide, bis(piperidido)titanium dibromide, bis(pyrrolidido)titanium dibromide, bis(pyrroleyl)titanium dibromide, bis(N-methylcyclohexylamido)titanium dibromide, bis(N-methylanilido)titanium dibromide, bis(N-ethylanilido)titanium dibromide, bis(N-propylanilido)titanium dibromide, bis(N-butylanilido)titanium dibromide, bis((N-methyl)toluylamido)titanium dibromide, bis((N-ethyl)toluylamido)titanium dibromide, bis((N-propyl)toluylamido)titanium dibromide, bis((N-butyl)toluylamido)titanium dibromide, bis((N-methyl)dimethylphenylamido)titanium dibromide, bis((N-ethyl)dimethylphenylamido)titanium dibromide, bis((N-propyl)dimethylphenylamido)titanium dibromide, bis((N-butyl)dimethylphenylamido)

titanium dichloride, bis(diphenylamido)titanium dibromide, bis((N-phenyl)toluylamido)titanium dibromide, bis(ditoluylamido)titanium dibromide, N,N'-diphenylmethylenediamidotitanium dibromide, N,N'-diphenylethylenediamidotitanium dibromide, N,N'-diphenylpropylenediamidotitanium dibromide, bis(dimethylamido)zirconium dibromide, bis(diethylamido)zirconium dibromide, bis(dipropylamido)zirconium dibromide, bis(dibutylamido)zirconium dibromide, bis((N-methyl)ethylamido)zirconium dibromide, bis((N-methyl)propylamido)zirconium dibromide, bis((N-methyl)butylamido)zirconium dibromide, bis((N-ethyl)propylamido)zirconium dibromide, bis((N-ethyl)butylamido)zirconium dibromide, bis(piperidido)zirconium dibromide, bis(pyrrolidido)zirconium dibromide, bis(pyrroleyl)zirconium dibromide, bis(N-methylcyclohexylamido)zirconium dibromide, bis(N-methylanilido)zirconium dibromide, bis(N-ethylanilido)zirconium dibromide, bis(N-propylanilido)zirconium dibromide, bis(N-butylanilido)zirconium dibromide, bis((N-methyl)toluylamido)zirconium dibromide, bis((N-ethyl)toluylamido)zirconium dibromide, bis((N-propyl)toluylamido)zirconium dibromide, bis((N-butyl)toluylamido)zirconium dibromide, bis((N-methyl)dimethylphenylamido)zirconium dibromide, bis((N-ethyl)dimethylphenylamido)zirconium dibromide, bis((N-propyl)dimethylphenylamido)zirconium dibromide, bis((N-butyl)dimethylphenylamido)zirconium dibromide, bis(diphenylamido)zirconium dibromide, bis((N-phenyl)toluylamido)zirconium dibromide, bis(ditoluylamido)zirconium dibromide, N,N'-diphenylmethylenediamidozirconium dibromide, N,N'-diphenylethylenediamidozirconium dibromide, N,N'-diphenylpropylenediamidozirconium dibromide, bis(dimethylamido)hafnium dibromide, bis(diethylamido)hafnium dibromide, bis(dipropylamido)hafnium dibromide, bis(dibutylamido)hafnium dibromide, bis((N-methyl)ethylamido)hafnium dibromide, bis((N-methyl)propylamido)hafnium dibromide, bis((N-methyl)butylamido)hafnium dibromide, bis((N-ethyl)propylamido)hafnium dibromide, bis((N-ethyl)butylamido)hafnium dibromide, bis(piperidido)hafnium dibromide, bis(pyrrolidido)hafnium dibromide, bis(pyrroleyl)hafnium dibromide, bis(N-methylcyclohexylamido)hafnium dibromide, bis(N-methylanilido)hafnium dibromide, bis(N-ethylanilido)hafnium dibromide, bis(N-propylanilido)hafnium dibromide, bis(N-butylanilido)hafnium dibromide, bis((N-methyl)toluylamido)hafnium dibromide, bis((N-ethyl)toluylamido)hafnium dibromide, bis((N-propyl)toluylamido)hafnium dibromide, bis((N-butyl)toluylamido)hafnium dibromide, bis((N-methyl)dimethylphenylamido)hafnium dibromide, bis((N-ethyl)dimethylphenylamido)hafnium dibromide, bis((N-propyl)dimethylphenylamido)hafnium dibromide, bis((N-butyl)dimethylphenylamido)hafnium dibromide, bis(diphenylamido)hafnium dibromide, bis((N-phenyl)toluylamido)hafnium dibromide, bis(ditoluylamido)hafnium dibromide, N,N'-diphenylmethylenediamidohafnium dibromide, N,N'-diphenylethylenediamidohafnium dibromide and N,N'-diphenylpropylenediamidohafnium dibromide, or compounds of which a nitrogen atom of the above compounds is replaced by a phosphorus atom, bis(methoxyde) titanium difluoride, bis(ethoxyde)titanium difluoride, bis(propoxyde)titanium difluoride, bis(butoxyde)titanium difluoride, bis(phenoxyde)titanium difluoride, bis(methylphenoxyde) titanium difluoride, bis(naphtoxyde) titanium difluoride, bis(methoxyde) titanium dichloride, bis(ethoxyde)titanium dichloride, bis(propoxyde) titanium dichloride, bis(butoxyde) titanium dichloride, bis(phenoxyde)titanium dichloride, bis(methylphenoxyde) titanium dichloride, bis(naphtoxyde)titanium dichloride, bis(methoxyde)titanium dibromide, bis(ethoxyde)titanium dibromide, bis(propoxyde)titanium dibromide, bis(butoxyde)titanium dibromide, bis(phenoxyde)titanium dibromide, bis(methylphenoxyde)titanium dibromide, bis(naphtoxyde)titanium dibromide, bis(methoxyde)zirconium difluoride, bis(ethoxyde) zirconium difluoride, bis(propoxyde) zirconium difluoride, bis(butoxyde) zirconium difluoride, bis(phenoxyde) zirconium difluoride, bis(methylphenoxyde) zirconium difluoride, bis(naphtoxyde) zirconium difluoride, bis(methoxyde)zirconium dichloride, bis(ethoxyde) zirconium dichloride, bis(propoxyde) zirconium dichloride, bis(butoxyde) zirconium dichloride, bis(phenoxyde) zirconium dichloride, bis(methylphenoxyde) zirconium dichloride, bis(naphtoxyde) zirconium dichloride, bis(methoxyde)zirconium dibromide, bis(ethoxyde) zirconium dibromide, bis(propoxyde) zirconium dibromide, bis(butoxyde) zirconium dibromide, bis(phenoxyde) zirconium dibromide, bis(methylphenoxyde) zirconium dibromide, bis(naphtoxyde) zirconium dibromide, bis(methoxyde) hafnium difluoride, bis(ethoxyde) hafnium difluoride, bis(propoxyde) hafnium difluoride, bis(butoxyde) hafnium difluoride, bis(phenoxyde) hafnium difluoride, bis(methylphenoxyde) hafnium difluoride, bis(naphtoxyde) hafnium difluoride, bis(methoxyde) hafnium dichloride, bis(ethoxyde) hafnium dichloride, bis(propoxyde) hafnium dichloride, bis(butoxyde) hafnium dichloride, bis(phenoxyde) hafnium dichloride, bis(methylphenoxyde) hafnium dichloride, bis(naphtoxyde) hafnium dichloride, bis(methoxyde) hafnium dibromide, bis(ethoxyde) hafnium dibromide, bis(propoxyde) hafnium dibromide, bis(butoxyde) hafnium dibromide, bis(phenoxyde) hafnium dibromide, bis(methylphenoxyde) hafnium dibromide, bis(naphtoxyde) hafnium dibromide, or compounds of which an oxygen atom of the above compounds is replaced by a sulfur atom. Among these, the synthesis of the compounds, wherein a $(R_m-A)$ group is a dimethylamide, diethylamide or diphenylamide groups, X is a halogen atom, is carried out by converting a tetrahalogenometal compound to a tetrakisamidometal compound, followed by the disproportionation of the tetrahalogenometal compound and the tetrakisamidometal compound in solvent (JP, B, 42-22691; Organometallics, 13, 2907 (1994); Z. Anorg. Allg. Chem., 621, 2021, (1995)), and the synthesis of the compounds, wherein a $(R_m-A)$ group is a isopropoxyl group, and X is a halogen atom, is also carried out by the disproportionation (Spectrochimica Acta., 24A, 1213 (1968)).

Further, by the reaction of the tetrahalogenometal compound and 2 equivalent mol. of $(R_m-A)^-(M^2)^+$(the below Reaction Scheme 3), the compounds of the general formula (I) can be synthesized in high yields.

Reaction scheme 3

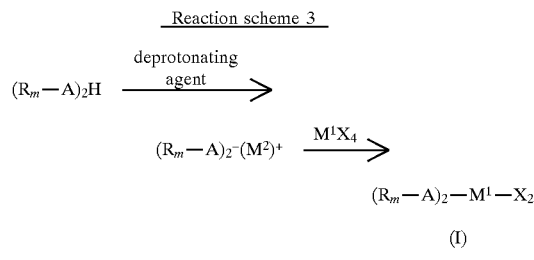

The various kinds of compounds represented by the general formula (II) and (II') have been hitherto synthesized as starting materials for the synthesis of metallocene compounds. Illustrative of $L^1$ and $L^2$ constituting the general formula (II) and (II') are, for example, a cyclopentadienyl, 3-methylcyclopentadienyl, 2,4-dimethylcyclopentadienyl, 3-tert-butylcyclopentadienyl, 2,3,4,5-tetramethylcyclopentadienyl, indenyl, 2-methylindenyl, 2-methyl-4,5-benzoindenyl, 2-methyl-4-phenylindenyl, 2-methyl-4-naphthylindenyl, fluorenyl or 2,7-di-tert-butylfluorenyl groups, or the like. Additionally, illustrative of B constituting the compounds represented by the general formula (II) and (II') are, for example, a methylene, ethylene, isopropylidene, diphenylmethylene, dimethylsilylene or diphenylsilylene groups, or the like.

In compounds represented by the general formula (III) and (III') produced by reacting a compound of the general formula (I) with a compound of either the general formula (II) or (II') is theoretically considered the case that the structural isomers are involved according to the structure of the general formula (II) or (II'). For example, a mixture of metallocene compounds having a racemic or meso structures should be obtained in the case that the 2 and 3 positions and the 4 and 5 positions of cyclopentadiene ring are not symmetric and $L^1$ and $L^2$ are of the same structure. However, to be surprised, in the reaction of a compound of the general formula (I) and a compound of the general formula (II'), the generation of metallocene compounds having the meso structure and tarry substances are suppressed, and metallocene compounds of the general formula (III') having the racemic structure can be synthesized efficiently and selectively.

As a synthetic method of the compounds of the general formula (II) and (II'), for an example, a ligand of the general formula $(L^1)H—B—(L^2)H$ is cooled and added with a deprotonating agent in solvent, followed by stirring at room temperature for 30 min. to overnight to give them. Illustrative of the deprotonating agent are alkaline metals or alkaline earth metals such as Li, Na, K, LiH, NaH, KH, MeLi, n-BuLi, sec-BuLi or tert-BuLi, or solution thereof dissolved in organic solvents such as n-hexane, cyclohexane or diethyl ether, or the like. The complex formation reaction is carried out by dissolving or suspending a compound of the general formula (I) in solvent, followed by adding a solution of a compound of the general formula (II) or (II'). The reaction does not require a special heating and is carried out under stirring at room temperature for 30 min. to overnight. Usually, the reaction is completed for such a short time as 30 min.–3 hours. Illustrative of the solvent used in the deprotonation and the complex formation are THF, diethyl ether, diisopropyl ether, toluene or the like, preferably THF, diethyl ether or diisopropyl ether. The metallocene compounds of the general formula (III) or (III') having the racemic structure can be obtained by removing the salts produced as byproducts in the reaction. The compounds of the general formula (III) and (III') are expected to be able to show the efficiency as an olefin polymerization catalyst under the coexistence of a cocatalyst such as aluminoxane.

The compounds of the general formula (III) and (III') can be convertible to the dihalogenated metallocene compounds of the general formula (IV) and (IV') which are conventionally used as an olefin polymerization catalyst. Illustrative of the compounds of the general formula (IV) and (IV') are dimethylsilylenebis(cyclopentadienyl)titanium dichloride, ethylenebis(1-indenyl)titanium dichloride, diphenylsilylenebis(fluorenyl)titanium dichloride, dimethylsilylenebis(cyclopentadienyl)zirconium dichloride, ethylenebis(1-indenyl)zirconium dichloride, diphenylsilylenebis(fluorenyl)zirconium dichloride, dimethylsilylenebis(cyclopentadienyl)hafnium dichloride, ethylenebis(1-indenyl)hafnium dichloride and diphenylsilylenebis(fluorenyl)hafnium dichloride, etc. Up to date are known the examples that ethylenebis(indenyl) zirconium bis(dimethylamide) and dimethysilylenebis (indenyl)zirconium bis(dimethylamide) are chlorinated by using $Me_3SiCl$ or $Me_2NH.HCl$ (WO 95/32979; U.S. Pat. No. 5,495,035; *Organometallics*, 14, 5 (1995); 211*th American Chemical Society National Meeting, Division of Polymer Chemistry Inc.* 251; *J. Am. Chem. Soc.*, 118, 8024 (1996)). It has also been known that o-xylenebis(1-indenyl) zirconium dimethyl, cis-1,4-bis(1-indenyl)-2-butendiyl zirconium dimethyl and ethylenebis(1-indenyl)zirconium dimethyl are chlorized by Hcl gas (*J. Organomet. Chem.*, 535, 29 (1997)). However, any example in which the other compounds are halogenated has not been known. The halogenation is carried out by dissolving a metallocene compound of the general formula (III) or (III') in solvent and adding a halogenating agent at –78° C.~room temperature, followed by stirring to afford the metallocene compounds of the general formula (IV) or (IV'). As a halogenating agent can be used $Me_2NH.HCl$, HCl gas, conc. HCl or $Me_3SiCl$, or the like. Solvents such as THF, toluene, chloroform, methylene chloride, trichloromethane, carbon tetrachloride, chlorobenzene or dichlorobenzene, or the like can be used.

In the following, the invention will be explained in more concrete way by examples, referential examples and comparative examples, but it is to be understood that the invention is not limited thereby in any way. Further, all reactions in the examples were performed under an inert gas atmosphere of an Ar or $N_2$ gases or the like. Additionally, solvents used in the reactions were dried and degassed.

REFERENTIAL EXAMPLE 1

Synthesis of bis(N-methylanilido)zirconium dichloride.bistetrahydrofuran

N-Methylaniline (40.0 g) and THF (233 ml) were placed in a 1 liter Schlenk tube and cooled to 0° C. Subsequently, the mixture was dropped with a n-BuLi/n-hexane solution (1.68N, 233 ml) at the same temperature in 15 min, warmed to room temperature and stirred for 3.5 hours. Another 1 liter Schlenk tube prepared separately was charged with THF (160 ml) and $ZrCl_4.2THF$ (70.5 g), whereby the mixture was then dropped with the anion of N-methylaniline under stirring in 1 hour and stirred at room temperature for 3 hours. After the reaction, the solvent was distilled under reduced pressure to give the viscous liquid, which was extracted with methylene chloride (500 ml) to remove the insoluble LiCl. The solution was concentrated under reduced pressure to remove the solvent, followed by collecting precipitated crystals to give bis(N-methylanilido)zirconium dichloride- .bistetrahydrofuran (77.0 g, 79% yield, yellowpowder) The analytical data are as follows, confirming the title compound.

$^1$H-NMR (90 MHz, $CDCl_3$/TMS) δ (ppm) 1.7–1.9 (m, THF, 8H), 3.36 (s, NMe, 6H), 4.0–4.2 (m, THF, 8H), 6.6–7.3 (m, phenyl, 10H).

Elemental analysis: Found. C, 49.90%; H, 6.088%; N, 5.326%. Calcd. C, 50.95%; H, 6.219%; N, 5.401%.

REFERENTIAL EXAMPLE 2

Synthesis of bis(N-methylanilido)hafnium dichloride.bistetrahydrofuran

N-Methylaniline (4.98 g) and THF (29 ml) were placed in a 100 ml Schlenk tube and cooled to 0° C. Subsequently, the mixture was dropped with a n-BuLi/n-hexane solution (1.68N, 29.1 ml) at the same temperature in 1 min, warmed to room temperature and stirred overnight. Another 200 ml Schlenk tube prepared separately was charged with n-pentane (20 ml) and HfCl$_4$ (7.45 g). The mixture was cooled to −80° C. and added with THF (40 ml) under stirring, while it was warmed to room temperature. It was dropped with the anion of N-methylaniline in 15 min. under stirring and stirred at room temperature for 1 hour. After the reaction, the solvent was distilled under reduced pressure to give the viscous liquid, which was extracted with methylene chloride (50 ml) to remove the insoluble LiCl. The solution was concentrated under reduced pressure to remove the solvent, followed by collecting precipitated crystals to give bis(N-methylanilido)hafnium dichloride.bistetrahydrofuran (10.4 g, 74% yield, white crystals). The analytical data are as follows, confirming the title compound.

$^1$H-NMR (90 MHz, CDCl$_3$/TMS) δ (ppm) 1.75–1.90 (m, THF, 8H), 3.35 (s, NMe, 6H), 4.02–4.16 (m, THF, 8H), 6.6–7.4 (m, phenyl, 10H).

REFERENTIAL EXAMPLE 3

Synthesis of bis(N-ethylanilido)zirconium dichloride.bistetrahydrofuran

N-Ethylaniline (10.0 g) and THF (155 ml) were placed in a 300 ml Schlenk tube and cooled to 0°C. Subsequently, the mixture was dropped with a n-BuLi/n-hexane solution (1.68N, 51.6 ml) at the same temperature in 2 min, warmed to room temperature and stirred for 3 hours. Another 500 ml Schlenk tube prepared separately was charged with THF (60 ml) and ZrCl$_4$.2THF (15.6 g), whereby the mixture was then dropped with the anion of N-ethylaniline under stirring in 10 min. and stirred at room temperature for half an hour. After the reaction, the solvent was distilled under reduced pressure to give the viscous liquid, which was extracted with methylene chloride (100 ml) to remove the insoluble LiCl. The solution was concentrated under reduced pressure to remove the solvent, followed by collecting precipitated crystals to give bis(N-ethylanilido)zirconium dichloride.bistetrahydrofuran (16.3 g, 72% yield, yellow powder). The analytical data are as follows, confirming the title compound.

$^1$H-NMR (90 MHz, CDCl$_3$/TMS) δ (ppm) 1.05 (t, J=7.03 Hz, CH$_3$, 3H), 1.25 (t, J=7.03 Hz, CH$_3$, 3H), 1.81 (m, THF, 8H), 3.15 (q, J=7.03 Hz, CH$_2$, 2H), 3.19 (q, J=7.03 Hz, CH$_2$, 2H), 3.93 (m, THF, 8H), 6.6–7.3 (m, phenyl, 10H).

Elemental analysis: Found. C, 51.23%; H, 6.462%; N, 5.250%. Calcd. C, 52.73%; H, 6.637%; N, 5.124%.

REFERENTIAL EXAMPLE 4

Synthesis of N,N'-diphenylethylenediamidozirconium dichloride.bistetrahydrofuran 1,2-Dianilinoethane (5.0 g) and THF (58 ml) were placed in a 100 ml Schlenk tube and cooled to 0° C. Subsequently, the mixture was dropped with a n-BuLi/n-hexane solution (1.68N, 28.8 ml) at the same temperature in 2 min, warmed to room temperature and stirred for 2 hours. Another 100 ml Schlenk tube prepared separately was charged with THF (5.8 ml) and ZrCl$_4$.2THF (8.90 g), whereby the mixture was then dropped with the anion of 1,2-dianilinoethane under stirring in 5 min. and stirred at room temperature overnight. After the reaction, the solvent was distilled under reduced pressure to give the viscous liquid, which was extracted with methylene chloride (60 ml) to remove the insoluble LiCl. The solution was concentrated under reduced pressure to remove the solvent, giving N,N'-diphenylethylenediamidozirconium dichloride.bistetrahydrofuran (12.5 g, 102% yield, yellow powder). The analytical data are as follows, confirming the title compound.

$^1$H-NMR (90 MHz, CDCl$_3$/TMS) δ (ppm) 1.6–2.0 (m, THF, 8H), 3.4–4.0 (m, THF, Et, 12H), 6.6–7.6 (m, phenyl, 10H).

REFERENTIAL EXAMPLE 5

Synthesis of bis(pyrroleyl)zirconium dichloride.bistetrahydrofuran

Pyrrole (7.0 ml) and THF (191 ml) were placed in a 300 ml Schlenk tube and cooled to 0° C. Subsequently, the mixture was dropped with a n-BuLi/n-hexane solution (1.66N, 63.9 ml) at the same temperature in 10 min., warmed to room temperature and stirred overnight. Another 300 ml Schlenk tube prepared separately was charged with THF (30 ml), n-pentane (15 ml) and ZrCl$_4$.2THF (19.1 g), whereby the mixture was then dropped with the anion of pyrrole under stirring in 35 min. and stirred at room temperature overnight. After the reaction, the solvent was distilled under reduced pressure to give the viscous liquid, which was extracted with methylene chloride (100 ml) to remove the insoluble LiCl. The solution was concentrated under reduced pressure to remove the solvent, giving bis(pyrroleyl)zirconium dichloride.bistetrahydrofuran (22.3 g, 101% yield, a brown viscous paste). The analytical data are as follows, confirming the title compound.

$^1$H-NMR (400 MHz, CDCl$_3$/TMS) δ (ppm) 1.8–2.1 (broad, THF, 8H), 3.6–4.3 (broad, THF, 8H), 5.91–5.97 (m, CH$_2$, 4H), 7.19–7.23 (m, CH$_2$, 4H).

REFERENTIAL EXAMPLE 6

Synthesis of bis(dimethylamido)zirconium dichloride.bistetrahydrofuran

Tetrakis(dimethylamido)zirconium (2.19 g), THF (10 ml) and diethyl ether (20 ml) were placed in a 50 ml Schlenk tube to obtain the solution. Another 50 ml Schlenk tube prepared separately was charged with ZrCl$_4$.2THF (3.10 g) and THF (20 ml) and, whereby the mixture was then dropped with the tetrakis (dimethylamido) zirconium solution under stirring in 1 min. and stirred at room temperature overnight. After the reaction, the solvent was distilled under reduced pressure to give bis(dimethylamido)zirconium dichloride.bistetrahydrofuran (5.97 g, 92% yield, pale yellow powder). The analytical data are as follows, confirming the title compound.

$^1$H-NMR (400 MHz, CDCl$_3$/TMS) δ (ppm) 1.8–2.0 (broad, THF, 8H), 3.11 (s, NMe$_2$, 12H), 3.5–4.7 (broad, THF, 8H).

REFERENTIAL EXAMPLE 7

Synthesis of bis(phenoxido)zirconium dichloride.bistetrahydrofuran

Phenol (2.45 g) and THF (17 ml) were placed in a 1000 ml Schlenk tube and cooled to 0° C. Subsequently, the mixture was dropped with a n-BuLi/n-hexane solution (1.66N, 17.3 ml) at the same temperature in 3 min., warmed to room temperature and stirred for 5.5 hours. Another 100 ml Schlenk tube prepared separately was charged with THF (15 ml), n-pentane (15 ml) and ZrCl$_4$.2THF (4.91 g), whereby the mixture was then dropped with the anion of phenol under stirring in 10 min. and stirred at room temperature overnight. After the reaction, the solvent was distilled under reduced pressure to give the viscous liquid, which was extracted with methylene chloride (60 ml) to remove the insoluble LiCl. The solution was concentrated under reduced pressure to remove the solvent, giving bis (phenoxido)zirconium dichloride.bistetrahydrofuran (5.74 g, 90% yield, a red-brown viscous paste). The analytical data are as follows, confirming the title compound.

$^1$H-NMR (400 MHz, CDCl$_3$/TMS) δ (ppm) 1.7–2.2 (broad, THF, 8H), 3.5–4.7 (broad, THF, 8H), 6.8–7.3 (m, Ph, 10H).

EXAMPLE 1

Synthesis of isopropylidenebis(2-indenyl)zirconium bis(N-methylanilide)

Isopropylidenebis(2-indene) (0.420 g) and THF (9.7 ml) were placed in a 50 ml Schlenk tube and cooled to 0° C. Subsequently, the mixture was was dropped with a n-BuLi/ n-hexane solution (1.66N, 1.94 ml) in 10 seconds and stirred at room temperature for 3 hours. Another 50 ml Schlenk tube prepared separately was charged with bis(N-methylanilido) zirconium dichloride.bistetrahydrofuran (0.799 g) and THF (5.0 ml), whereby the mixture was then dropped with the anion of isopropylidenebis(2-indene) under stirring in 20 seconds and stirred at room temperature for half an hour, followed by removing the solvent under reduced pressure to give the red-brown liquid, which was washed with n-pentane (30 ml), extracted with methylene chloride (30 ml) to remove the insoluble LiCl. The solution was distilled under reduced pressure to remove the solvent to give isopropylidenebis(2-indenyl)zirconium bis(N-methylanilide) (0.711 g, 80% yield based of bis (methylanilido)zirconium dichloride.bistetrahydrofuran) as red-brown powder. The analytical data are as follows, confirming the title compound.

$^1$H-NMR (90 MHz, CDCl$_3$/TMS) δ (ppm) 1.97 (s, isopropylidene, 6H), 2.35 (s, NMe, 6H), 6.16 (s, C$_5$ring, 4H), 6.4–7.5 (m, C$_6$ring, 18H).

Comparative example 1

Reaction employing ZrCl$_4$

Isopropylidenebis(2-indene) (0.25 g) and diethyl ether (5.0 ml) were placed in a 20 ml Schlenk tube and cooled to 0°0 C. Subsequently, the mixture was dropped with a n-BuLi/n-hexane solution (1.60N, 1.2 ml) and stirred at room temperature for 4 hours. The stirring was stopped to let the anion precipitate. After removing the supernatant, the precipitate was washed with n-pentane (14 ml), added with methylene chloride (15 ml), cooled to −78° C., added with ZrCl$_4$ (0.225 g), warmed slowly under stirring to room temperature and stirred overnight. The $^1$H-NMR analysis of the reaction solution could not confirm the aimed product in the products.

EXAMPLE 2

Synthesis of rac-ethylenebis(1-indenyl)zirconium bis(N-methylanilide)

1,2-Bis(3-indenyl)ethane (3.01 g) and THF (45.8 ml) were placed in a 100 ml Schlenk tube and cooled to 0° C. Subsequently, the mixture was dropped with a n-BuLi/n-hexane solution (1.57N, 15.2 ml) in 5 min. and stirred at room temperature for 1 hour. Another 200 ml Schlenk tube prepared separately was charged with bis(N-methylanilido) zirconium dichloride.bistetrahydrofuran (6.35 g) and THF (45.8 ml), whereby the mixture was then dropped with the anion of 1,2-bis(3-indenyl)ethane under stirring in 5min. and stirred at room temperature for 1 hour. The $^1$H-NMR analysis showed that the reaction proceeded in a more than 95% racemic selectivity. The solvent was distilled under reduced pressure to give the red-brown powder, which was extracted with methylene chloride (100 ml) to remove the insoluble LiCl. The solution was evaporated under reduced pressure to give rac-ethylenebis(1-indenyl)zirconium bis(N-methylanilide) (6.39 g, 98% yield based on 1,2-bis(3-indenyl)ethane) as red-brown powder. The analytical data are as follows, confirming the title compound.

$^1$H-NMR (90 MHz, CDCl$_3$/TMS) δ (ppm) 2.65 (s, NMe, 6H), 3.55–3.91 (m, Et, 4H), 5.95 (dd, J=3.30 Hz, J=0.88 Hz, C$_5$ring, 2H), 6.24 (d, J=3.30 Hz, C$_5$ring, 2H), 6.45–7.39 (m, C$_6$ring, 16H), 7.79 (ddd, J=0.88 Hz, J=8.35 Hz, J=0.88 Hz, C$_6$ring, 2H)

EXAMPLE 3

Synthesis of rac-ethylenebis(1-indenyl)zirconium bis(N-ethylanilide)

1,2-Bis(3-indenyl)ethane (1.54 g) and THF (22.0 ml) were placed in a 100 ml Schlenk tube and cooled to 0° C. Subsequently, the mixture was dropped with a n-BuLi/n-hexane solution (1.68N, 7.45 ml) in 20 seconds and stirred at room temperature for 1.5 hours. Another 100 ml Schlenk tube prepared separately was charged with bis(N-ethylanilido)zirconium dichloride.bistetrahydrofuran (3.26 g) and THF (11.0 ml), whereby the mixture was then dropped with the anion of 1,2-bis(3-indenyl)ethane under stirring in 2 min. and stirred at room temperature for 2 hours. The $^1$H-NMR analysis showed that the reaction proceeded in a more than 95% racemic selectivity. The solvent was distilled under reduced pressure to give the red-brown powder, which was extracted with methylene chloride (60 ml) to remove the insoluble LiCl. The solution was evaporated under reduced pressure to give rac-ethylenebis(1-indenyl)zirconium bis(N-ethylanilide) (4.14 g, 118% yield based on bis(N-ethylanilido)zirconium dichloride.bistetrahydrofuran) as red-brown powder. The analytical data are as follows, confirming the title compound.

$^1$H-NMR (90 MHz, CDCl$_3$/TMS) δ (ppm) 0.71 (t, J=6.81 Hz, CH$_3$, 6H), 3.22 (q, J=6.81 Hz, CH$_2$, 4H), 3.73 (m, Et, 4H), 5.89 (dd, J=3.29 Hz, J=0.87 Hz, C$_5$ring, 2H), 5.96 (d, J=3.29 Hz, C$_5$ring, 2H), 6.55 (dd, J=8.57 Hz, J=1.54 Hz, C$_6$ring, 2H), 6.74–7.26 (m, C$_6$ring, 14H), 7.84 (ddd, J=0.88 Hz, J=8.57 Hz, J=0.88 Hz, C$_6$ring, 2H).

EXAMPLE 4

Synthesis of rac-dimethylsilylenebis(1-indenyl) zirconium bis(N-methylanilide)

Dimethylsilylenebis(1-indene) (0.449 g) and THF (10 ml) were placed in a 50 ml Schlenk tube and cooled to 0° C. Subsequently, the mixture was dropped with a n-BuLi/n-hexane solution (1.57N, 2.08 ml) in 20 seconds and stirred at room temperature for 3 hours. Another 100 ml Schlenk tube prepared separately was charged with bis(N-methylanilido)zirconium dichloride.bistetrahydrofuran (0.811 g) and THF (15 ml), whereby the mixture was then dropped with the anion of dimethylsilylenebis(1-indene) under stirring in 2 min. and stirred at room temperature for 4 hours. The $^1$H-NMR analysis showed that the reaction proceeded in a more than 95% racemic selectivity. The solvent was distilled under reduced pressure to give the red-brown powder, which was extracted with methylene chloride (30 ml) to remove the insoluble LiCl. The solution was evaporated under reduced pressure to give rac-dimethylsilylenebis(1-indenyl)zirconium bis(N-methylanilide) (0.976 g, 106% yield based on bis(N-methylanilido)zirconium dichloride.bistetrahydrofuran) as red-brown powder. The analytical data are as follows, confirming the title compound.

$^1$H-NMR (90 MHz, CDCl$_3$/TMS) δ (ppm) 1.16 (s, Si-Me, 6H), 2.53 (s, NMe, 6H), 6.34–7.85 (m, C$_6$ring, 22H)

EXAMPLE 5

Synthesis of rac-ethylenebis(1-indenyl)hafnium bis (N-methylanilide)

1,2-Bis(3-indenyl)ethane (1.84 g) and THF (30 ml) were placed in a 100 ml Schlenk tube and cooled to 0° C. Subsequently, the mixture was dropped with a n-BuLi/n-hexane solution (1.68N, 8.88 ml) in 20 seconds and stirred at room temperature for 1.5 hours. Another 100 ml Schlenk tube prepared separately was charged with bis(N-methylanilido) hafnium dichloride.bistetrahydrofuran (4.30 g) and THF (20 ml), whereby the mixture was then dropped with the anion of 1,2-bis(3-indenyl)ethane under stirring in 3 min. and stirred at room temperature for half an hour. The $^1$H-NMR analysis showed that the reaction proceeded in a more than 95% racemic selectivity. The solvent was distilled under reduced pressure to give the red-brown powder, which was extracted with methylene chloride (60 ml) to remove the insoluble LiCl. The solution was evaporated under reduced pressure to give rac-ethylenebis(1-indenyl)hafnium bis(N-methylanilide) (4.62 g, 101% yield based on bis(N-methylanilido)hafnium dichloride.bistetrahydrofuran) as pale orange powder. The analytical data are as follows, confirming the title compound.

$^1$H-NMR (90 MHz, CDCl$_3$/TMS) δ (ppm) 2.70 (s, NMe, 6H), 3.78 (s, Et, 4H), 5.86 (dd, J=3.07 Hz, J=0.88 Hz, C$_5$ring, 2H), 6.11 (d, J=3.07 Hz, C$_5$ring, 2H), 6.32 (dd, J=8.57 Hz, J=1.31 Hz, C$_6$ring, 2H), 6.46–7.45 (m, C$_6$ring, 14H), 7.86 (ddd, J=0.88 Hz, J=8.57 Hz, J=1.10 Hz, C$_6$ring, 2H).

EXAMPLE 6

Synthesis of rac-ethylenebis(1-indenyl)zirconium bis(N,N'-diphenylethylenediamide)

1,2-Bis(3-indenyl)ethane (1.42 g) and THF (21 ml) were placed in a 100 ml Schlenk tube and cooled to 0° C. Subsequently, the mixture was dropped with a n-BuLi/n-hexane solution (1.68N, 6.85 ml) in 20 seconds and stirred at room temperature for 1.5 hours. Another 50 ml Schlenk tube prepared separately was charged with N,N'-diphenylethylenediamidozirconium dichloride.bistetrahydrofuran (2.83 g) and THF (10 ml), whereby the mixture was then dropped with the anion of 1,2-bis(3-indenyl)ethane under stirring in 2 min. and stirred at room temperature for 3.5 hours. The $^1$H-NMR analysis showed that the reaction proceeded in a more than 95% racemic selectivity. The solvent was distilled under reduced pressure to give the red-brown powder, which was extracted with methylene chloride (40 ml) to remove the insoluble LiCl. The solution was evaporated under reduced pressure to give rac-ethylenebis(1-indenyl)zirconium bis(N,N'-diphenylethylenediamide) (3.40 g, 111% yield based on N,N'-diphenylethylenediamidozirconium dichloride.bistetrahydrofuran) as brown powder. The analytical data are as follows, confirming the title compound.

$^1$H-NMR (90 MHz, CDCl$_3$/TMS) δ (ppm) 3.23–3.73 (m, Et, 8H), 6.08 (dd, J=1.32 Hz, J=1.10 Hz, C$_5$ring, 2H), 6.16 (d, J=1.32 Hz, C$_5$ring, 2H), 6.52–7.53 (m, C$_6$ring, 18H).

EXAMPLE 7

Synthesis of dimethylsilylenebis(2-methyl-4,5-benzoindenyl)zirconium bis(pyrroleyl)

Dimethylsilylenebis(2-methyl-4,5-benzoindene) (0.870 g) and THF (7.9 ml) were placed in a 100 ml Schlenk tube and cooled to 0° C. Subsequently, the mixture was dropped with a n-BuLi/n-hexane solution (1.66N, 2.6 ml) in 5 seconds and stirred at room temperature for 2 hours. The reaction mixture was dropped with a bis(pyrroleyl) zirconium dichloride.bistetrahydrofuran (0.916 g) solution in THF (3.3 ml) in 5 seconds and stirred at room temperature for 4.5 hours. After the reaction, the solvent was evaporated under reduced pressure to give the dark green powder, which was extracted with methylene chloride (30 ml) to remove LiCl. The solvent was evaporated under reduced pressure, giving dimethylsilylenebis(2-methyl-4,5-benzoindenyl) zirconium bis(pyrroleyl) (1.55 g, brown powder, 116% yield based on bis(pyrroleyl)zirconium dichloride.bistetrahydrofuran).

EXAMPLE 8

Synthesis of rac-ethylenebis(1-indenyl)zirconium bis(dimethylamide)

1,2-Bis(3-indenyl)ethane (0.721 g) and THF (10.6 ml) were placed in a 50 ml Schlenk tube and cooled to 0° C. Subsequently, the mixture was dropped with a n-BuLi/n-hexane solution (1.66N, 3.5 ml) in 20 seconds and stirred at room temperature overnight. The reaction mixture was dropped with a bis(dimethylamido)zirconium dichloride.bistetrahydrofuran (0.699 g) solution in THF (5.5 ml) in 30 seconds and stirred at room temperature for 9 hours. Then, the $^1$H-NMR analysis showed that the reaction proceeded in a more than 95% racemic selectivity. The solvent was evaporated under reduced pressure to give the orange powder, which was extracted with methylene chloride (30 ml) to remove LiCl. The solvent was evaporated under reduced pressure to give rac-ethylenebis(1-indenyl) zirconium bis(dimethylamide) (1.08 g, 89% yield based on bis(dimethylamido)zirconium dichloride.bistetrahydrofuran) as orange powder. The analytical data are as follows, confirming the title compound.

$^1$H-NMR (400 MHz, CDCl$_3$/TMS) δ (ppm) 2.42 (s, N—Me, 12H), 3.5 (m, Et, 4H), 6.05 (d, J=3.17 Hz, C$_5$ring, 2H), 6.38 (d, J=3.17 Hz, C$_5$ring, 2H), 6.80 (t, C$_6$ring, 2H), 7.05 (t, C$_6$ring, 2H), 7.24 (d, C$_6$ring, 2H), 7.67 (d, C$_6$ring, 2H).

EXAMPLE 9

Synthesis of ethylenebis(1-indenyl)zirconium bis (phenoxide)

1,2-bis(3-indenyl)ethane (0.721 g) and THF (11.3 ml) were placed in a 50 ml Schlenk tube and cooled to 0° C. Subsequently, the mixture was dropped with a n-BuLi/n-hexane solution (1.66N, 3.8 ml) in 20 seconds and stirred at room temperature for 2 hours. The reaction mixture was dropped with a bis(phenoxido)zirconium dichloride.bistetrahydrofuran (1.39 g) solution in THF (12.1 ml) in 5 seconds and stirred at room temperature overnight. After the reaction, the solvent was evaporated under reduced pressure to give the red powder, which was extracted with methylene chloride (30 ml) to remove LiCl. The solvent was evaporated under reduced pressure, giving ethylenebis(1-indenyl) zirconium bis(phenoxide) (1.56 g, yellow powder, 103% yield based on bis(phenoxido)zirconium dichloride.bistetrahydrofuran). The analytical data are as follows, confirming the title compound.

$^1$H-NMR (400 MHz, CDCl$_3$/TMS) δ (ppm) 3.82 (m, Et, 4H), 6.09 (d, C$_5$ring, 2H), 6.22 (d, C$_5$ring, 2H), 6.7–7.3 (m, C$_6$ring, 16H), 7.86 (d, C$_6$ring, 2H).

EXAMPLE 10

Synthesis of rac-ethylenebis(1-indenyl)zirconium dichloride rac-Ethylenebis(1-indenyl)zirconium bis(N-methylanilide) (6.39 g) and methylene chloride (250 ml) were placed in a 500 ml Schlenk tube and cooled to −78° C. Subsequently, the mixture was bubbled slowly with HCl gas, whereby the color of the solution turned from red to yellow, and then, the introduction of HCl gas was stopped. The mixture was concentrated under reduced pressure and recrystallized to give rac-ethylenebis(1-indenyl)zirconium dichloride (3.0 g, 62% yield based on 1,2-bis(3-indenyl) ethane). The analytical data are as follows, confirming the title compound.

$^1$H-NMR (90 MHz, CDCl$_3$/TMS) δ (ppm) 3.75 (s, Et, 4H), 6.20 (d, J=3.30 Hz, C$_5$ring, 2H), 6.58 (dd, J=3.30 Hz, J=0.88 Hz, C$_5$ring, 2H), 7.1–7.7 (m, C$_6$ring, 8H).

EXAMPLE 11

Synthesis of rac-ethylenebis(1-indenyl)zirconium dichloride rac-Ethylenebis(1-indenyl)zirconium bis(N-ethylanilide) (4.14 g) and methylene chloride (30 ml) were placed in a 100 ml Schlenk tube and cooled to −78° C. Subsequently, the mixture was bubbled slowly with HCl gas, whereby the color of the solution turned from red to yellow, and then, the introduction of HCl gas was stopped. The mixture was concentrated under reduced pressure and recrystallized to give rac-ethylenebis(1-indenyl)zirconium dichloride (1.11 g, 45% yield based on bis(N-ethylanilido)zirconium dichloride.bistetrahydrofuran). The analytical data are as follows, confirming the title compound.

$^1$H-NMR (90 MHz, CDCl$_3$/TMS) δ (ppm) 3.75 (s, Et, 4H), 6.20 (d, J=3.30 Hz, C$_5$ring, 2H), 6.58 (dd, J=3.30 Hz, J=0.88 Hz, C$_5$ring, 2H), 7.1–7.7 (m, C$_6$ring, 8H).

EXAMPLE 12

Synthesis of rac-dimethylsilylenebis(1-indenyl) zirconium dichloride rac-Dimethylsilylenebis(1-indenyl)zirconium bis(N-methylanilide) (0.976 g) and methylene chloride (10 ml) were placed in a 50 ml Schlenk tube and cooled to −78° C. Subsequently, the mixture was bubbled slowly with HCl gas, whereby the color of the solution turned from red to yellow, and then, the introduction of HCl gas was stopped. The mixture was concentrated under reduced pressure and recrystallized to give rac-ethylenebis(1-indenyl)zirconium dichloride (0.381 g, 54% yield based on bis(N-methylanilido)zirconium dichloride.bistetrahydrofuran). The analytical data are as follows, confirming the title compound.

$^1$H-NMR (90 MHz, CDCl$_3$/TMS) δ (ppm) 1.14 (s, Si-Me, 6H), 6.11 (d, J=3.30 Hz, C$_5$ring, 2H), 6.83 (dd, J=3.30 Hz, J=0.88 Hz, C$_5$ring, 2H), 7.0–7.7 (m, C$_6$ring, 8H).

EXAMPLE 13

Synthesis of rac-ethylenebis(1-indenyl)hafnium dichloride rac-Ethylenebis(1-indenyl)hafnium bis(N-methylanilide) (4.62 g) and methylene chloride (20 ml) were placed in a 50 ml Schlenk tube and cooled to −78° C. Subsequently, the mixture was bubbled slowly with HCl gas, whereby the color of the solution turned from orange to yellow, and then, the introduction of HCl gas was stopped. The mixture was concentrated under reduced pressure and recrystallized to give rac-ethylenebis(1-indenyl) hafnium dichloride (1.84 g, 51% yield based on bis(N-methylanilido)hafnium dichloride.bistetrahydrofuran). The analytical data are as follows, confirming the title compound.

$^1$H-NMR (90 MHz, CDCl$_3$/TMS) δ (ppm) 3.80 (s, Et, 4H), 6.10 (d, J=3.30 Hz, C$_5$ring, 2H), 6.47 (dd, J=3.30 Hz, J=0.88 Hz, C$_5$ring, 2H), 7.1–7.7 (m, C$_6$ring, 8H).

EXAMPLE 14

Synthesis of rac-ethylenebis(1-indenyl)zirconium dichloride rac-Ethylenebis(1-indenyl)zirconium bis(N,N'-diphenylethylenediamide) (3.40 g) and methylene chloride (30 ml) were placed in a 50 ml Schlenk tube and cooled to −78° C. Subsequently, the mixture was bubbled slowly with HCl gas, whereby the color of the solution turned from orange to yellow, and then, the introduction of HCl gas was stopped. The mixture was concentrated under reduced pressure and recrystallized to give rac-ethylenebis(1-indenyl) zirconium dichloride (0.652 g, 28% yield based on N,N'-diphenylethylenediamidozirconium dichloride.bistetrahydrofuran). The analytical data are as follows, confirming the title compound.

$^1$H-NMR (90 MHz, CDCl$_3$/TMS) δ (ppm) 3.75 (s, Et, 4H), 6.20 (d, J=3.30 Hz, C$_5$ring, 2H), 6.58 (dd, J=3.30 Hz, J=0.88 Hz, C$_5$ring, 2H), 7.1–7.7 (m, C$_6$ring, 8H).

EXAMPLE 15

Synthesis of rac-dimethylsilylenebis(2-methyl-4,5-benzoindenyl)zirconium dichloride Dimethylsilylenebis(2-methyl-4,5-benzoindenyl) zirconium bis(pyrroleyl) (1.55 g) and methylene chloride (10 ml) were placed in a 50 ml Schlenk tube and cooled to −78° C. Subsequently, the mixture was bubbled slowly with HCl gas, whereby the color of the solution turned from brown to orange, and then, the introduction of HCl gas was stopped. The mixture was concentrated under reduced pressure and recrystallized to give dimethylsilylenebis(2-methyl-4, 5-benzoindenyl)zirconium dichloride (0.192 g, 16% yield based on bis(pyrroleyl)zirconium dichloride.bistetrahydrofuran) with the racemic ratio not less than 90%. The analytical data are as follows, confirming the title compound.

$^1$H-NMR (400 MHz, CDCl$_3$/TMS) δ (ppm) 1.36 (s, Si-Me, 6H), 2.37 (s, Indene-Me, 6H), 7.37–7.96 (m, C$_5$ring C$_6$ring, 14H)

EXAMPLE 16

Synthesis of rac-ethylenebis(1-indenyl)zirconium dichloride rac-Ethylenebis(1-indenyl)zirconium bis(dimethylamide) (1.08 g) and methylene chloride (20 ml) were placed in a 50 ml Schlenk tube and cooled to −78° C. Subsequently, the mixture was bubbled slowly with HCl gas, whereby the color of the solution turned from red to yellow, and then, the introduction of HCl gas was stopped. The mixture was concentrated under reduced pressure and recrystallized to give rac-ethylenebis(1-indenyl)zirconium dichloride (0.512 g, 44% yield based on bis(dimethylamido)zirconium dichloride.bistetrahydrofuran). The analytical data are as follows, confirming the title compound.

$^1$H-NMR (400 MHz, CDCl$_3$/TMS) δ (ppm) 3.75 (m, Et, 4H), 6.21 (d, J=3.42 Hz, C$_5$ring, 2H), 6.59 (d, J=3.42 Hz, C$_5$ring, 2H), 7.18–7.35 (m, C$_6$ring, 4H),7.49 (dd, J=0.73 Hz, J=8.54 Hz, C$_6$ring, 2H), 7.66 (ddd, J=0.73 Hz, J=0.73 Hz, J=8.54 Hz, C$_6$ring, 2H).

EXAMPLE 17

Synthesis of ethylenebis(1-indenyl)zirconium dichloride

Ethylenebis(1-indenyl)zirconium bis(phenoxide) (1.56 g), methylene chloride (10 ml) and diethyl ether (15 ml) were placed in a 50 ml Schlenk tube and cooled to −78° C. The mixture was dropped with a MeLi/diethyl ether solution (1.05 mol/l, 5.7 ml) in 1 min. and stirred at room temperature overnight. After removing the precipitated lithium phenoxide, the solvent was replaced by methylenechloride (30 ml) and the mixture was cooled to −78° C. Subsequently, the mixture was bubbled slowly with HCl gas, whereby the color of the solution turned from red to yellow, and then, the introduction of HCl gas was stopped. The mixture was concentrated under reduced pressure and recrystallized to give ethylenebis(1-indenyl)zirconium dichloride in which the ratio of the racemic form to the meso form is 50:50. The analytical data are as follows, confirming the title compound.

$^1$H-NMR (400 MHz, CDCl$_3$/TMS) δ (ppm) 3.65 (m, meso-Et, 2H), 3.75 (m, rac-Et, 4H), 3.95 (m, meso-Et, 2H), 6.21 (d, J=3.42 Hz, rac-C$_5$ring, 2H), 6.55 (d, J=3.42 Hz, meso-C$_5$ring, 2H), 6.59 (d, J=3.42 Hz, rac-C$_5$ring, 2H), 6.70 (d, J=3.42 Hz, meso-C$_5$ring, 2H), 7.1–7.5 (m, meso-C$_6$ring, 8H), 7.18–7.35 (m, rac-C$_6$ring, 4H), 7.49 (dd, J=0.73 Hz, J=8.54 Hz, rac-C$_6$ring, 2H), 7.66 (ddd, J=0.73 Hz, J=0.73 Hz, J=8.54 Hz, rac-C$_6$ring, 2H).

What is claimed is:

1. Process for synthesizing metallocene compounds of formula (III), said method comprising reacting a group IV transition-metal compound of formula (I)

wherein M$^1$ is a IV group transition-metal atom; each A is independently a hetero atom; each R is independently a hydrocarbon group having 1–30 carbon atoms; each R can, optionally, be bound to one another to form a ring containing A, or, optionally, a ring containing A and M$^1$; each X is independently a halogen atom or an alkoxy group having 1–10 carbon atoms; m is 1 or 2; and wherein M$^1$ can be coordinated with an ether or an amine at any available coordination site, with a compound of formula (II)

wherein L$^1$ and L$^2$ are independently selected from the group consisting of cyclopentadienyl, substituted cyclopentadienyl, indenyl, substituted indenyl, fluorenyl and substituted fluorenyl; B is a member selected from the group consisting of hydrocarbon having 1–20 carbon atoms, silylene having 1–20 carbon atoms, oligosilylene and germylene; and M$^2$ is member selected from the group consisting of an alkaline metal or an alkaline earth metal; wherein M$_2$ can be coordinated with an ether or an amine at any available coordination site to afford metallocene compounds of formula (III)

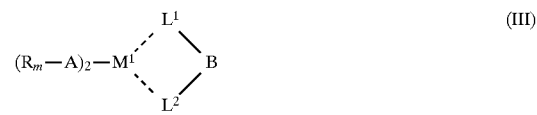

wherein M$^1$, A, R, B, L$^1$, L$^2$, and m are as defined above.

2. Process according to claim 1 wherein each X is a halogen atom.

3. Process according to claim 1 wherein A is a member selected from the group consisting of nitrogen, oxygen, phosphorus or sulfur.

4. Process according to claim 1 wherein A is nitrogen.

5. Process for synthesizing halogenated metallocene compounds of formula (IV), said method comprising halogenating a compound of formula (III)

wherein M$^1$ is a group IV transition-metal atom; each A is independently a hetero atom; each R is independently a hydrocarbon group having 1–30 carbon atoms; each R can, optionally, be bound to one another to form a ring containing A, or, optionally, a ring containing A and M$^1$; L$^1$ and L$^2$ are independently selected from the group consisting of cyclopentadienyl, indenyl, substituted indenyl, fluorenyl and substituted fluorenyl groups; B is a member selected from the group consisting of hydrocarbon having 1–20 carbon atoms, silylene having 1–20 carbon atoms, oligosilylene and germylene groups; m is 1 or 2; and wherein M$^1$ can be coordinated with an ether or an amine at any available coordination site, to afford a compound of formula (IV)

wherein M$^1$, A, R, B, L$^1$, L$^2$, and m are as defined above, and each Y is independently a halogen atom;

with the proviso that compounds of formula (III) cannot be ethylenebis(indenyl)zirconium bis(dimethylamide), dimethylsilylenebis(indenyl)zirconium bis(dimethylamide), dimethylsilylenebis(2-methyl-4-tert-butylcyclopentadienyl)zirconium bis(dimethylamide), or dimethylsilylenebis(2-methyl-4-tert-butylcyclopentadienyl)zirconium bisdipyrrolidide.

6. Process for synthesizing metallocene compounds of formula (III') having a racemic structure comprising reacting a group IV transition-metal compound of formula (I)

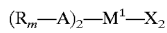

wherein $M^1$ is a IV group transition-metal atom; each A is independently a hetero atom; each R is independently a hydrocarbon group having 1–30 carbon atoms; each R can, optionally, be bound to one another to form a ring containing A, or, optionally, a ring containing A and $M^1$; each X is independently a halogen atom or an alkoxy group having 1–10 carbon atoms; m is 1 or 2; and wherein $M^1$ can be coordinated with an ether or an amine at any available coordination site, with a compound of formula(II')

$$(M^2)^+(L^1)^- - B - (L^2)^-(M^2)^+ \quad \text{(II')}$$

wherein $L^1$ and $L^2$ are independently selected from the group consisting of substituted cyclopentadienyl, indenyl, substituted indenyl and substituted fluorenyl groups; B is selected from the group consisting of hydrocarbon having 1–20 carbon atoms, silylene having 1–20 carbon atoms, oligosilylene and germylene; and $M^2$ is a member selected from the group consisting of alkaline metals and alkaline earth metals; wherein $M^2$ can be coordinated with an ether or an amine at any available coordination site, to afford a metallocene compound of formula (III')

wherein $M^1$, A, R, B, $L^1$, $L^2$, and m are as defined above.

7. Process according to claim 6 wherein each X in formula (I) is independently a halogen atom.

8. Process according to claim 6 wherein each A in formula (I) is independently a nitrogen, oxygen, phosphorus or sulfur atom.

9. Process according to claim 6 wherein each A in formula (I) is a nitrogen atom.

10. Process for synthesizing halogenated metallocene compounds of formula (IV') having a racemic structure comprising halogenating a compound of formula (III')

wherein $M^1$ is a group IV transition-metal atom, each A is independently a hetero atom; each R is independently selected from the group consisting of a hydrocarbon group having 1–30 carbon atoms; wherein each R can, optionally, be bound to one another to form a ring containing A, or, optionally, a ring containing A and $M^1$; $L^1$ and $L^2$ are independently selected from the group consisting of substituted cyclopentadienyl, indenyl, substituted indenyl and substituted fluorenyl groups; B is selected from the group consisting of hydrocarbon having 1–20 carbon atoms, silylene having 1–20 carbon atoms, oligosilylene and germylene; m is 1 or 2; wherein $M^1$ can be coordinated with an ether or an amine at any available coordination site, to afford a compound of formula (IV')

wherein $M^1$, A, B, R, $L^1$, $L^2$, and m are as defined above, and each Y is independently a halogen atom;

with the proviso that compounds of formula (III') cannot be ethylenebis(indenyl)zirconium bis(dimethylamide), dimethylsilylenebis(indenyl)zirconium bis(dimethylamide) dimethylsilylenebis(2-methyl-4-tert-butylcyclopentadienyl)zirconium bis(dimethylamide), or dimethylsilylenebis(2-methyl-4-tert-butylcyclopentadienyl)zirconium bisdipyrrolidide.

* * * * *

UNITED STATES PATENT AND TRADEMARK OFFICE
CERTIFICATE OF CORRECTION

PATENT NO. : 5,892,075
DATED : April 6, 1999
INVENTOR(S) : Kunihiko Murata et al.

It is certified that error appears in the above-identified patent and that said Letters Patent is hereby corrected as shown below:

Col. 22, line 12, change "$M_2$" to -- $M^2$ --.

Col. 22, line 56, change "$M^1, A, R, B, L^1, L^2$, and m" to -- $M^1, B, L^1, L^2$ --.

Col. 22, line 64, change "bisdipyrrolidide" to -- bispyrrolidide --.

Col. 24, line 31, change "$M^1, A, B, R, L^1, L^2$, and m" to -- $M^1, B, L^1, L^2$ --.

Col. 24, line 39, change "bisdipyrrolidide" to -- bispyrrolidide --.

Signed and Sealed this

Twenty-ninth Day of February, 2000

Attest:

Q. TODD DICKINSON

Attesting Officer

Commissioner of Patents and Trademarks